United States Patent
Ghosh et al.

(10) Patent No.: US 12,365,691 B2
(45) Date of Patent: Jul. 22, 2025

(54) METHOD OF SYNTHESIZING (3S,3AR,5R,7AS,8S)-HEXAHYDRO-4H-3,5-METHANOFURO[2,3-B]PYRAN-8-OL

(71) Applicant: Purdue Research Foundation, West Lafayette, IN (US)

(72) Inventors: Arun K. Ghosh, West Lafayette, IN (US); Shivaji Markad, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 59 days.

(21) Appl. No.: 18/298,226

(22) Filed: Apr. 10, 2023

(65) Prior Publication Data

US 2023/0399338 A1    Dec. 14, 2023

Related U.S. Application Data

(60) Provisional application No. 63/350,960, filed on Jun. 10, 2022.

(51) Int. Cl.
C07D 493/04    (2006.01)

(52) U.S. Cl.
CPC .................... C07D 493/04 (2013.01)

(58) Field of Classification Search
CPC .............................................. C07D 493/04
USPC ...................................................... 549/464
See application file for complete search history.

(56) References Cited

U.S. PATENT DOCUMENTS

2022/0363688 A1*  11/2022  Ghosh ................. C07D 493/08

FOREIGN PATENT DOCUMENTS

| WO | 2015175994 | 11/2015 |
| WO | 2022119858 | 6/2022 |
| WO | 2022251615 | 12/2022 |

OTHER PUBLICATIONS

Qabaja et al., Asymmetric Synthesis of Hydroxy Esters with Multiple Stereocenters via a Chiral Phosphoric Acid Catalyzed Kinetic Resolution, 2015, Journal of Organic Chemistry, vol. 80, pp. 133-140. (Year: 2015).*

"European Application Serial No. 23178284.8, Extended European Search Report mailed Oct. 30, 2023", 9 pgs.

"European Application Serial No. 23178284.8, Response filed Jun. 13, 2024 to Extended European Search Report mailed Oct. 30, 2023", 12 pgs.

"European Application Serial No. 23178284.8, Communication Pursuant to Article 94(3) EPC mailed Aug. 20, 2024", 4 pgs.

Ghosh, Arun K., "A convenient synthesis of (3S,3aR,5R,7aS,8S)-Hexahydro-4H-3,5-methan ofuro[2,3-b]pyran-8-ol, a high-affinity nonpeptidyl ligand for highly potent HIV-1 protease inhibitors", Tetrahedron Letters, Elsevier, Amsterdam , NL, vol. 109,, (Sep. 21, 2022), 5 pgs.

Gosh, A K, "Design and Development of highly potent HIV-1 protease inhibitors with a crown-like oxotricyclic core as the P2-ligand to combat multidrug-resistant HIV variants", Journal of Medicinal Chemistry, vol. 60, (Apr. 18, 2017), 4267-4278.

Marzijarani, Nastaran, "New Mechanism for Cinchona Alkaloid-Catalysis Allows for an Efficient Thiophosphorylation Reaction", J. Am. Chem. Soc. 2020, 142, 47, 20021-20029., (Nov. 12, 2020), 118 pgs.

* cited by examiner

*Primary Examiner* — Jeffrey H Murray
*Assistant Examiner* — Rilla Marie Samsell
(74) *Attorney, Agent, or Firm* — Schwegman Lundberg & Woessner, P.A.

(57) ABSTRACT

The disclosure relates to a method of synthesizing the high-affinity, non-petidyl ligand (3S,3aR,5R,7aS,8S)-hexahydro-4H-3,5-methanofuro[2,3-b]pyran-8-ol, which is useful in the synthesis of various compounds, such as HIV-1 protease inhibitors.

20 Claims, 4 Drawing Sheets

(3S,3aR,5R,7aS,8S)-hexahydro-
4H-3,5-methanofuro[2,3-b]pyran-8-ol

METHOD OF SYNTHESIZING (3S,3AR,5R,7AS,8S)-HEXAHYDRO-4H-3,5-METHANOFURO[2,3-B]PYRAN-8-OL

CROSS-REFERENCE TO RELATED APPLICATIONS

This application claims the benefit of U.S. Provisional Appl. Ser. No. 63/350,960, filed Jun. 10, 2022, which is incorporated by reference as if fully set forth herein.

STATEMENT OF GOVERNMENT SUPPORT

This invention was made with government support under A1150466 awarded by the National Institutes of Health. The government has certain rights in the invention.

BACKGROUND

Protein X-ray structure-based drug design has had a significant impact on preclinical drug discoveries in modern medicine. The structure-based drug design efforts often lead to innovative heterocycles with structural and stereochemical complexities. Many such successes are particularly notable in the design and development of HIV-1 protease inhibitor drugs and kinase inhibitor drugs. HIV-1 protease inhibitors (PIs) are critical elements of current antiretroviral therapies (cART), which have dramatically transformed HIV/AIDs from a fatal disease to a manageable chronic disorder. However, emergence of drug-resistant HIV-1 variants severely compromises the clinical benefits of PIs. In continuing efforts to combat drug resistance, PI design is particularly focused on promoting extensive hydrogen bonding interactions with backbone atoms throughout the active site. This has led to the design of a wide range of bicyclic, polyether-derived ligands that mimic peptide binding but do not contain any unwanted peptidyl features. Many PIs incorporating these bicyclic, polyether templates exhibit very potent activity, including broad-spectrum activity against multidrug-resistant HIV-1 variants. One of these PIs is Darunavir, an FDA-approved and widely used PI, which contains a fused, bicyclic bis-tetrahydrofuran (bis-THF) as a nonpeptidyl, high-affinity P2 ligand. The bis-THF heterocycle is a critically important pharmacophore that is responsible for Darunavir's durable, drug resistance profile. However, the emergence of Darunavir-resistant HIV-1 variants has been reported, and options for treating patients infected with such variants are limited. Therefore, the development of novel PIs with broad spectrum antiviral activity is urgently needed for future cART treatment options.

SUMMARY

In view of the above, it is an object of the present disclosure to provide a method of synthesizing a high-affinity P2 ligand, which is useful for the synthesis of HIV-1 protease inhibitors. The method employs inexpensive and commercially available starting materials, involves fewer steps than currently used methods of synthesis, and provides enantiomerically pure (e.g., 99%) ligand. Other objects and advantages, as well as inventive features, will be apparent from the detailed description provided herein.

Provided is an optically active synthesis of (3S,3aR,5R,7aS,8S)-hexahydro-4H-3,5-methanofuro[2,3-b]pyran-8-ol. This stereochemically defined 6-tricyclic heterocyclic compound is an important high-affinity P2 ligand for a variety of highly potent HIV-1 protease inhibitors with clinical potential. Important steps involve an enantioselective ring opening of meso carbic anhydride mediated by a Cinchona alkaloid, specifically quinidine. The resulting optically active acid is reduced to an optically active bicyclo[2.2.1]hept-5-ene derivative. The derivative is converted to a ligand alcohol by ozonolysis and reduction. The resulting primary alcohol is dehydrated. Optically active ligand alcohol is obtained in high enantiomeric purity (e.g., 99%) and can be converted to a potent HIV-1 protease inhibitor. The synthesis is efficient, and the overall protocol is useful for the preparation of a variety of structural derivatives.

DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Figure 1:
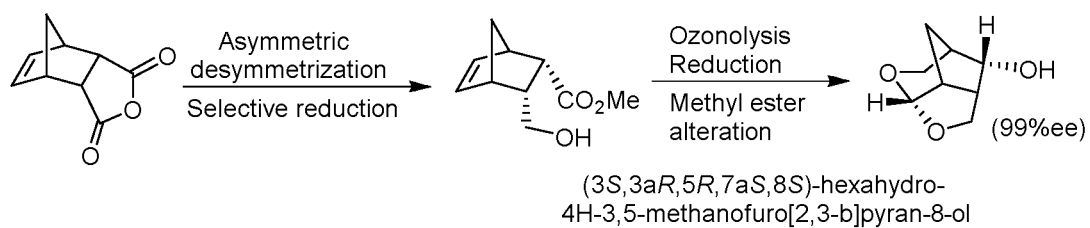
FIG. 1 is an overview of the chemical synthetic scheme.
Figure 2:
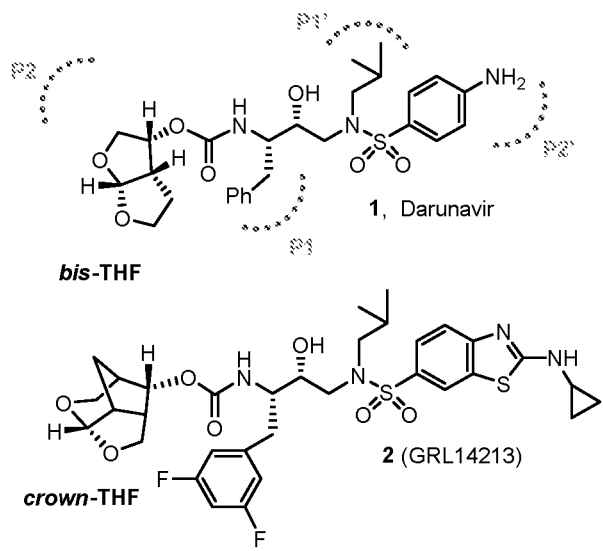
FIG. 2 shows structure of HIV-1 protease inhibitors (PIs) darunavir (1) and GRL14213 (2).

The present disclosure generally relates to a method of synthesizing a high-affinity, non-petidyl ligand, which is useful, for example, in the synthesis of HIV-1 protease inhibitors (e.g., highly potent HIV-1 protease inhibitors). Novel HIV-1 protease inhibitors (PIs) with much improved properties have been designed by fine-tuning Darunavir's ligand binding site interactions, based upon X-ray structures of DRV and other PI-bound HIV-1 protease.5,23 PI GRL-14213 (compound 2 in FIG. 2; see, also, International Patent Application Publication No. WO 2015/175994, compound I, paragraph [0056]) is exceedingly potent, exerting multiple modes of action including inhibition of catalytically active dimeric enzyme, inhibition of dimerization of protease, and inhibition of integrase function. This PI also has improved central nervous system penetration and exhibits a significantly higher selectivity index compared to Darunavir and other PI drugs. X-ray structural analysis of PI 2-bound HIV-1 protease revealed that the stereochemically defined hexahydro-4H-3,5-methanofuro[2,3-b]pyran-8-ol ligand makes stronger hydrogen bonding interactions with main-chain atoms in the S2 pocket. In addition, the extra methylene groups appear to make favorable van der Waals interactions with hydrophobic residues in the S2 subsite. This crown-like-THF (tetrahydrofuran) ligand contains a fused three-ring system with five contiguous chiral centers. Previous synthesis of the ligand involved an enantioselective Diels-Alder reaction of vinyl boronate and cyclopentadiene in the presence of a chiral oxazaborolidine catalyst. Asymmetric Diels-Alder reactions of cyclopentadiene with chiral 3-(acyloxy)acryloxazolidinone derivatives to furnish the key intermediate for the synthesis were also examined. In an effort to provide ready access to optically active ligand alcohol, an alternative synthetic route, which involves a Cinchona alkaloid-mediated enantioselective ring opening of meso carbic anhydride as the key reaction, was developed. The resulting, optically active carboxylic acid monoester has been converted to crown-THF ligands. The route is convenient and potentially amenable to the synthesis of other structural variants in optically active form. An optically active ligand alcohol can be converted to a potent PI 2 (FIG. 2).

The disclosure provides a method of making a compound of the formula (I):

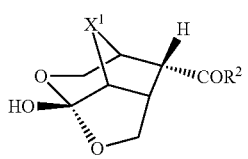

or a salt thereof, with an enantiomeric excess (ee) of at least 90% (e.g., at least 91%, at least 92%, at least 95%, at least 98%, at least 99%, from about 90% to about 94%, from about 93% to about 98% or from about 95% to about 99%); wherein:

$X^1$ is alkylene, —O—, —$CH_2NR^1$— or —$NHR^1$—, wherein $R^1$ is alkyl, aryl or heteroaryl, and $R^2$ is hydroxy, alkoxy or amido;

the method comprising (i) converting a compound of the formula (II):

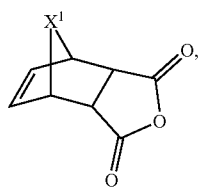

or a salt thereof,
to a compound of the formula (III):

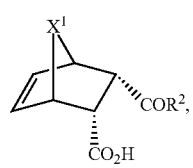

or a salt thereof;

(ii) converting the compound of formula (III), or a salt thereof, to a compound of the formula (IV):

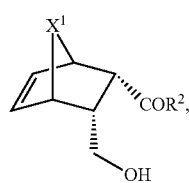

or a salt thereof; and (iii) converting the compound of formula (IV), or a salt thereof, to the compound of the formula (I). The converting in step (i) can comprise ring opening of the compound of the formula (II). Such a ring opening can be performed using any suitable means, including by using a Cinchona alkaloid, or a derivative thereof, such as quinidine and cinchonine, and derivatives thereof. See, e.g., *J. Am. Chem. Soc.* 2020, 142, 47, 20021-20029, which is incorporated by reference as if fully set forth herein. Alternatively or in addition, the converting in step (ii) can comprise reducing the compound of formula (III) to a compound of the formula (IV), or a salt thereof. Alternatively or in addition the converting in step (iii) can comprise cleaving the double bond of the compound of the formula (IV), or a salt thereof, by any suitable means including ozonolysis, periodate cleavage, and the like. When the converting in step (iii) comprises ozonolysis of the compound of formula (IV), or a salt thereof, an ozonolysis product, or a salt thereof is obtained. Alternatively or in addition, the methods of the disclosure can further comprise reducing the ozonolysis product, or a salt thereof, to obtain the compound of the formula (I). In one example, the ozonolysis product is of the formula (V):

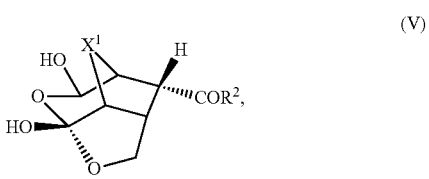

or a salt thereof.

In any of the compounds described herein, $X^1$ can be alkylene. Alternatively or in addition, the alkylene can be a $C_1$-$C_3$(alkylene) group, such as —$CH_2$— —$CH_2CH_2$—. In one example, $X^1$ is alkylene and $R^2$ is hydroxy. In another example, $X^1$ is —O—, such as where $X^1$ is —O— and $R^2$ is hydroxy.

The disclosure also provides a method of making a compound of the formula (VI):

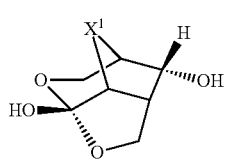

or a salt thereof, with an enantiomeric excess (ee) of at least 90% (e.g., at least 91%, at least 92%, at least 95%, at least 98%, at least 99%, from about 90% to about 94%, from about 93% to about 98% or from about 95% to about 99%);

wherein:

$X^1$ is alkylene, —O—, —$CH_2NR^1$— or —$NHR^1$—, wherein $R^1$ is alkyl, aryl or heteroaryl;

the method comprising:

(i) converting a compound of the formula (I):

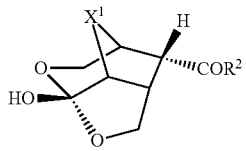
(I)

or a salt thereof,
wherein:

X¹ is alkylene, —O—, —CH₂NR¹— or —NHR¹—, wherein R¹ is alkyl, aryl or heteroaryl, and R² is hydroxy, alkoxy or amido, to a compound of the formula (VII):

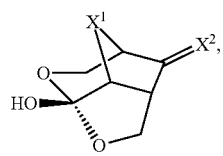
(VII)

or a salt thereof, wherein X² is O or CH₂; and (ii) converting the compound of formula (VII), or a salt thereof, to a compound of the formula (VI), or a salt thereof. The method can further comprise (iii) converting the compound of the formula (I) to a compound of the formula (VIII):

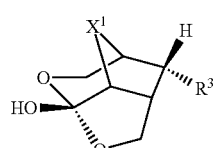
(VIII)

or a salt thereof,
wherein:

X¹ is alkylene, —O—, —CH₂NR¹— or —NHR¹—, wherein R¹ is alkyl, aryl or heteroaryl, and R³ is hydroxyalkyl or COR²; and (iv) converting the compound of the formula (VIII) to the compound of the formula(VII), wherein X² is CH₂. In one example, R³ is —CH₂OH. The method can further comprise (v) converting the compound of the formula (VII), or a salt thereof, wherein X² is CH₂ to the compound of the formula (VII), or a salt thereof, wherein X² is O. Again, in any of the compounds described herein, X¹ can be alkylene. Alternatively or in addition, the alkylene can be a C₁-C₃ (alkylene) group, such as —CH₂— —CH₂CH₂—. In one example, X¹ is —O—.

The methods of the disclosure can further comprise (vi) converting the compound of formula (VI), or a salt thereof, to a compound of the formula (IX):

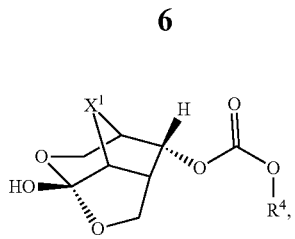
(IX)

or a salt thereof, wherein R⁴ is optionally substituted aryl. In addition, the method of the disclosure can further comprise conjugating the compound of the formula (IX), or a salt thereof, with a compound of the formula (X):

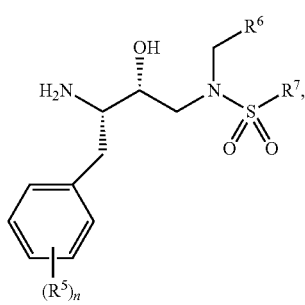

or a salt thereof, wherein:

n is an integer from 1 to 3;

R⁵ is alkoxy, hydroxyalkyl, halo or heterocyclylalkyloxy;

R⁶ is alkyl, haloalkyl, arylalkyl, cycloalkylalkyl, heterocyclylcarbonyl or heterocyclylalkyl; and R⁷ is aryl or heteroaryl, to give a compound of the formula (XI):

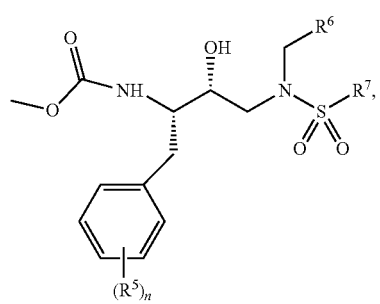

or a salt thereof. The compound of the formula (IX) can also be conjugated to form compounds useful to inhibit SARS-CoV-2. Such compounds are useful for the treatment of severe acute respiratory syndrome (SARS), similar to compounds like:

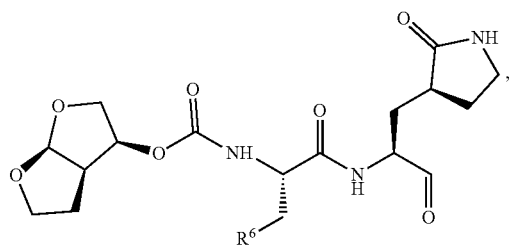

disclosed in WO2022/119858; and

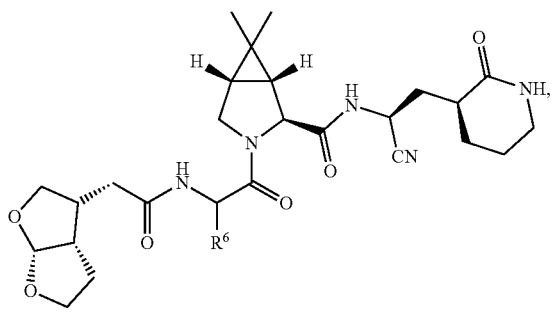

disclosed in WO2022/251615, both of which are incorporated by reference as if fully set forth herein. The bis-tetrahydrofuranyl group would be replaced by a group of the formula:

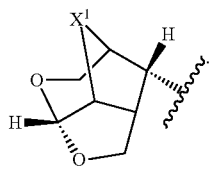

The disclosure also provides a method of making a compound of the formula (VIII):

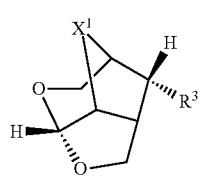

(VIII)

or a salt thereof, with an enantiomeric excess (ee) of at least 90% (e.g., at least 91%, at least 92%, at least 95%, at least 98%, at least 99%, from about 90% to about 94%, from about 93% to about 98% or from about 95% to about 99%); wherein:
$X^1$ is alkylene, —O—, —$CH_2NR^1$— or —$NHR^1$—, wherein $R^1$ is alkyl, aryl or heteroaryl, and
$R^3$ is hydroxyalkyl or $COR^2$;
the method comprising:
(i) converting a compound of the formula (I):

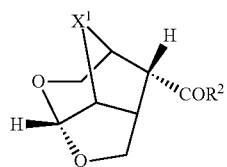

(I)

or a salt thereof,
wherein:
$X^1$ is alkylene, —O—, —$CH_2NR^1$— or —$NHR^1$—, wherein $R^1$ is alkyl, aryl or heteroaryl; and $R^2$ is hydroxy, alkoxy or amido,
to a compound of the formula (VIII).

Figure 3:
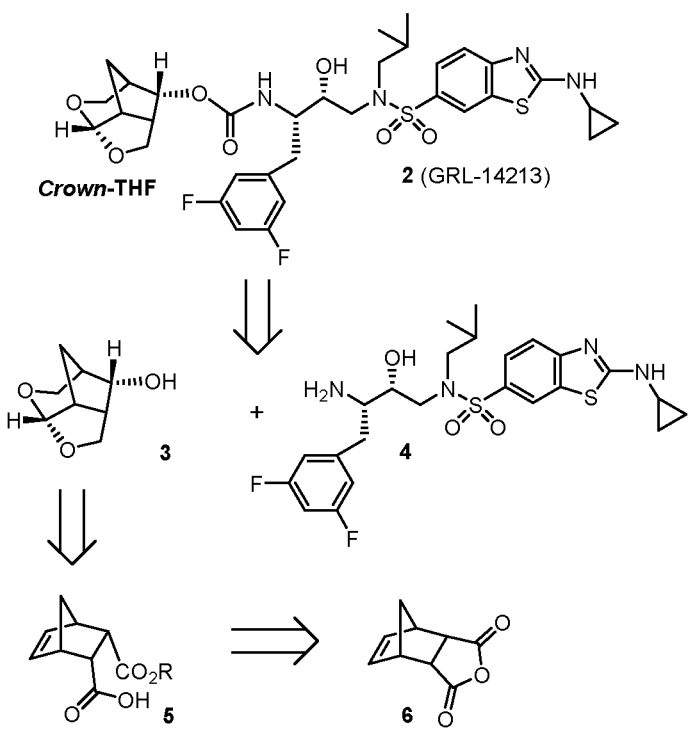
FIG. 3 shows the structures of the key building blocks for PI 2 and ligand 3.

An example of a synthetic plan for making the compounds described herein, such as those having optically active 6,5,5-tricyclic ligand alcohol 3, such as for PI 2, is shown in Scheme 1 (FIG. 3). The synthesis of stereochemically defined ligand alcohol 3 involves asymmetric desymmetrization of cyclic anhydride as a key step. Such an asymmetric strategy of Cinchona alkaloid-mediated ring opening of anhydrides in the presence of methanol has been investigated by Oda et al. The synthesis of alcohol 3 is carried out from the optically active tricyclic carboxylic acid derivative 5, which is obtained from meso-carbic anhydride 6.

Figure 4:
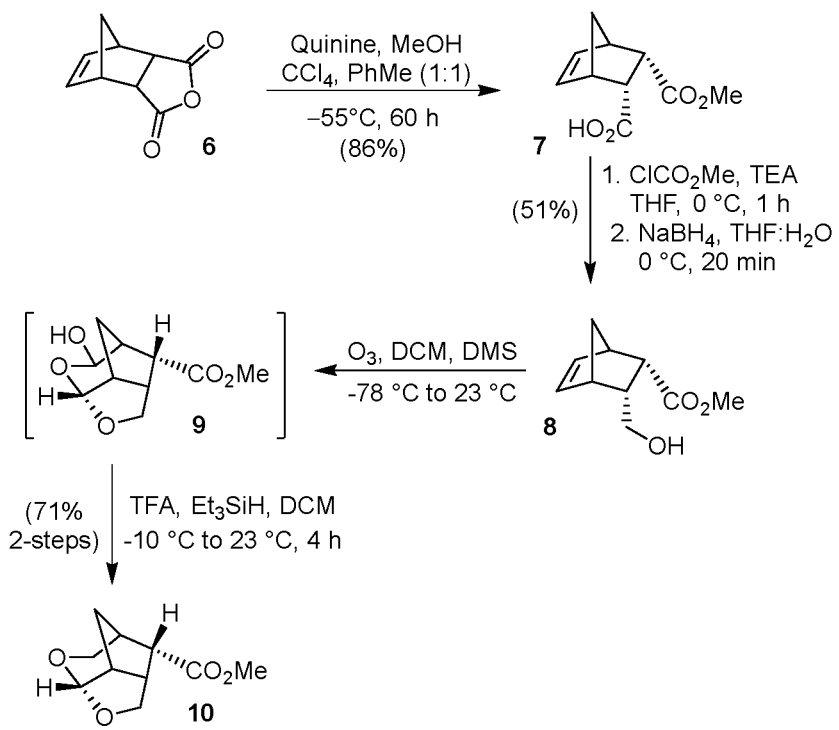
FIG. 4 shows the synthesis of optically active crown-THF (tetrahydrofuran) ester 10.

Asymmetric desymmetrization and synthesis of ligand alcohol are shown in Scheme 2 (FIG. 4). Reaction of carbic anhydride with a stoichiometric amount of quinidine in the presence of three equivalents of methanol in a 1:1 mixture of toluene and $CCl_4$ at −55° C. provides optically active carboxylic acid monoester 7 (e.g., in 86% yield in multigram scale). The resulting optically active monoester 7 sets four of the five contiguous chiral centers present in the ligand alcohol 3. Quinidine is fully recovered for reuse after the reaction. Monoester 7 is converted to alcohol 8 by formation of mixed anhydride with methylchloroformate and triethylamine in THF at 0° C. for 1 hour. The resulting anhydride is selectively reduced to alcohol using NaBH4 in aqueous THF at 0° C. for 20 minutes to provide 8 (e.g., in 51% yield) over two steps. To unravel the tetrahydrofuropyran functionality of ligand 3, alcohol 8 is exposed to ozonolytic cleavage in CH2Cl2 at −78° C. using dimethylsulfide to provide a mixture of hemiacetal 9. The resulting mixture of hemiacetal is exposed to triethylsilane (TES)-mediated reduction in the presence of trifluoroacetic acid in $CH_2Cl_2$ at −10° C. to 23° C. for 4 hours to provide tricyclic ester 10 (e.g., in 71% yield) over two steps. This ester may serve as a versatile intermediate for other functionalized ligands.

Figure 5:
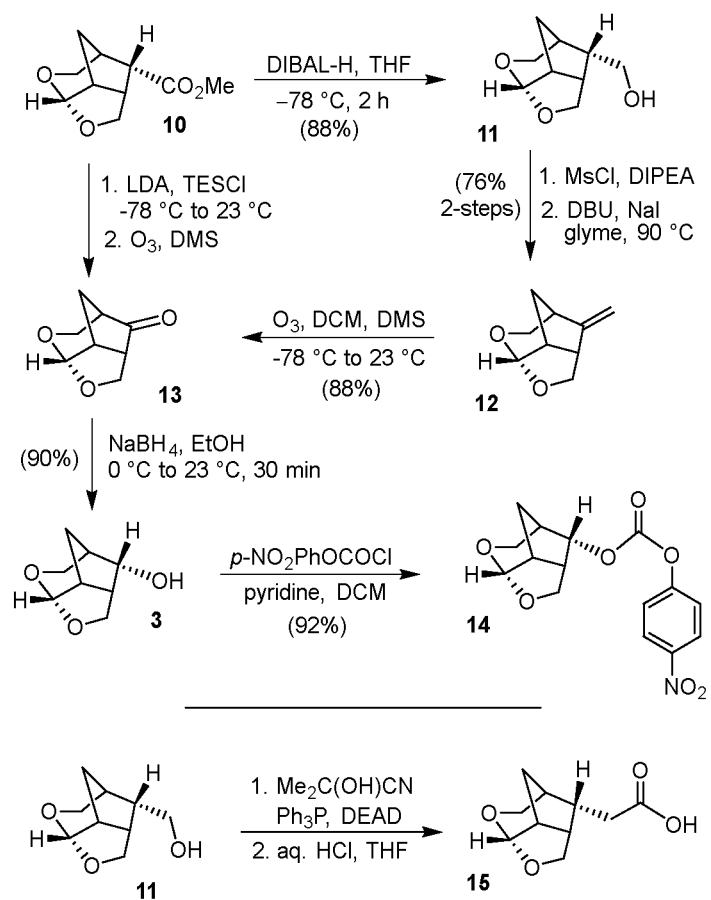
FIG. 5 shows the synthesis of optically active crown-THF ligands.

Methyl ester 10 is converted to ligand alcohol 3 as shown in Scheme 3 (FIG. 5). Dibal-H reduction of ester 10 at −78° C. for 2 hours furnishes alcohol 11 (e.g., in 88% yield). Alcohol 11 is converted to alkene 12 by mesylation with mesyl chloride and DIPEA (N,N-diisopropylethylamine) at 0° C. for 7 minutes, followed by reaction of the resulting mesylate with DBU (1,8-diazabicyclo(5.4.0)undec-7-ene) and NaI in glyme in a sealed tube at 90° C. for 3 hours to provide olefin 12 (e.g., in 76% yield) over two steps. Ozonolytic cleavage of 12 with dimethyl sulfide (DMS) at −78° C. to 23° C. for 8 hours provides ketone 13 (e.g., in 88% yield). Reduction of ketone 13 with NaBH4 in ethanol at 0° C. to 23° C. for 30 minutes provides ligand alcohol 3 as a single diastereomer (by $^1$H-NMR) (e.g., in 90% yield).

Ester 10 is also converted to ketone 13 in an alternative and shorter two-step route. Reaction of ester 10 with LDA (lithium diisopropylamide) and TESCI (chlorotriethylsilane) at −78° C. provides the corresponding silyl ketene acetal. Ozonolytic cleavage of the resulting silyl ketene acetal using DMS (dimethyl sulfide) provides ketone 13. Ligand alcohol 3 is converted to activated carbonate by treatment with 4-nitrophenyl chloroformate and DIPEA in DCM (dichloromethane) at 23° C. for 24 hours to furnish nitrocarbonate 14 (e.g., in 92% yield). Chiral HPLC analysis of 14 on a CHIRALPAK IC-3 column revealed an enantiomeric purity of 99% ee.

Alcohol 11 is also converted to carboxylic acid 15, which has been shown to be a high-affinity ligand for a number of amide-based, HIV-1 PIs. Thus, alcohol 11 is converted to the corresponding nitrile derivative by reaction with acetone cyanohydrin in the presence of diisopropylazodicarboxylate and triphenylphosphine. The resulting nitrile is treated with aqueous HCl at 50° C. for 12 hours to furnish the acid derivative 12.

Figure 6:
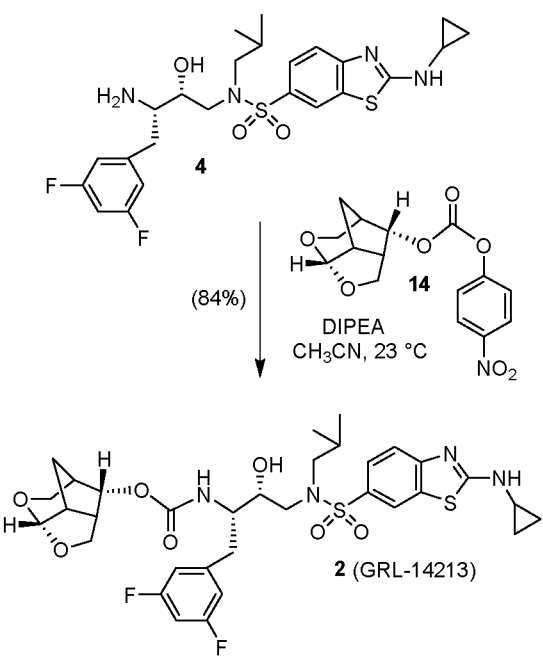
FIG. 6 shows the synthesis of potent PI 2.

Enantiomerically pure ligand alcohol 3 is converted into HIV-1 PI 2 as shown in Scheme 4 (FIG. 6). Reaction of the known (R)-(hydroxyethyl)sulfonamide isostere 4 with carbonate 14 in the presence of DIPEA at 23° C. for 5 days furnished HIV-1 PI 2 (e.g., in 84% yield). Inhibitor 2 displayed a $K_i$ value of 14 pM in HIV-1 protease inhibitory assay34 and displayed an antiviral $IC_{50}$ value of 17 pM in MT-2 human-T-lymphoid cells exposed to $HIV_{LAI}$.

Thus, hexahydro-4H-3,5-methanofuro[2,3-b]pyran-8-ol 3 in optically active form is conveniently synthesized using commercially available, inexpensive carbic anhydride. This ligand alcohol is the subunit of exceptionally potent PI 2, which exhibits unprecedented multiple modes of action. The key step involves an enantioselective ring opening of meso-carbic anhydride using a Cinchona alkaloid. The resulting optically active carboxylic acid monoester 5 contains four contiguous chiral centers, which were manipulated for the installation of all five chiral centers in the ligand alcohol. Selective reduction of acid 5, ozonolytic cleavage of olefin, and oxecarbenium ion-mediated silane reduction furnished a 6-5-5-fused tricyclic ester 10, which can be maneuvered for the synthesis of other functionalized ligands. Ester 10 was efficiently converted to ligand alcohol 3 and carboxylic acid 15. One advantage of the current synthetic route is the practical enantioselective synthesis from readily available meso-carbic anhydride and rapid entry to ligand alcohol in high optical purity. Ligand alcohol 3 was efficiently converted to PI 2. The route has the potential for scale-up. PI 2 is an exceptionally potent compound with preclinical potential. The current synthesis may offer convenient access to quantities of this class of PIs.

Any compound described herein can be a salt, such as a pharmaceutically acceptable salt. Examples of acceptable salts include, without limitation, alkali metal (for example, sodium, potassium or lithium) or alkaline earth metals (for example, calcium) salts; however, any salt that is generally non-toxic and effective when administered to the subject being treated is acceptable. Similarly, "pharmaceutically acceptable salt" refers to those salts with counter ions, which may be used in pharmaceuticals. Such salts may include, without limitation, (1) acid addition salts, which can be obtained by reaction of the free base of the parent compound with inorganic acids, such as hydrochloric acid, hydrobromic acid, nitric acid, phosphoric acid, sulfuric acid, perchloric acid, and the like, or with organic acids, such as acetic acid, oxalic acid, (D) or (L) malic acid, maleic acid, methane sulfonic acid, ethane sulfonic acid, p-toluene sulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion, or coordinates with an organic base, such as ethanolamine, diethanolamine, triethanolamine, trimethamine, N-methylglucamine, and the like. Pharmaceutically acceptable salts are well-known to those skilled in the art, and any such pharmaceutically acceptable salts are contemplated.

Acceptable salts can be obtained using standard procedures known in the art, including (without limitation) reacting a sufficiently acidic compound with a suitable base affording a physiologically acceptable anion. Suitable acid addition salts are formed from acids that form non-toxic salts. Illustrative, albeit nonlimiting, examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts of the compounds can be formed from bases that form non-toxic salts. Illustrative, albeit nonlimiting, examples include the arginine, benzathine, calcium, choline, diethylamine, diolamine, glycine, lysine, magnesium, meglumine, olamine, potassium, sodium, tromethamine and zinc salts. Hemi-salts of acids and bases, such as hemi-sulphate and hemi-calcium salts, also can be formed.

One of ordinary skill in the art will further appreciate that the above compounds can be "deuterated," meaning one or more hydrogen atoms can be replaced with deuterium. As deuterium and hydrogen have nearly the same physical properties, deuterium substitution is the smallest structural change that can be made.

The compounds, in some embodiments, can and do contain one or more asymmetric centers and thus give rise to enantiomers, diastereomers, and other stereoisomeric forms that are defined, in terms of absolute stereochemistry, as (R) or (S). Unless stated otherwise, it is intended that all stereoisomeric forms of the compounds are contemplated. When the conjugates contain alkene double bonds, and unless specified otherwise, it is intended that both E and Z geometric isomers (e.g., cis or trans) are included. Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

Further provided is a pharmaceutical composition comprising an above-described compound and a pharmaceutically acceptable carrier or excipient. The term "composition" generally refers to any product comprising more than one ingredient, including the compound. It is to be understood that the compositions can be prepared from isolated compounds or from salts, solutions, hydrates, solvates, and other forms of the compounds. It is appreciated that certain functional groups, such as the hydroxy, amino, and like groups can form complexes with water and/or various solvents, in the various physical forms of the compound. It is also to be understood that the compositions can be prepared from various amorphous, non-amorphous, partially crystalline, crystalline, and/or other morphological forms of the compounds, and the compositions can be prepared from various hydrates and/or solvates of the compounds. Accordingly, such pharmaceutical compositions can include each of, or any combination of, or individual forms of, the various morphological forms and/or solvate or hydrate forms of the compounds.

Any pharmaceutically acceptable carriers and excipients as known in the art can be used. A pharmaceutically acceptable carrier can include a solvent, dispersion medium, a coating, an antibacterial and/or antifungal agent(s), an isotonic and/or absorption delaying agent(s), and the like, and combinations thereof, that are physiologically compatible. The carrier can be suitable for parenteral administration, e.g., a sterile aqueous solution or dispersion or a sterile powder for the extemporaneous preparation of a sterile injectable solution or dispersion.

Examples of various ingredients include, but are not limited to, a color additive, a preservative, and a stabilizer. More specific examples include crystal cellulose, calcium carmellose, sodium carmellose, hydropropylcellulose, hydroxypropylmethylcellulose, ethylcellulose, and magnesium stearate. Such compositions can be manufactured in accordance with methods in the art and described, for example, in Remington, The Science and Practice of Pharmacy, 22nd edition. Supplementary active compounds can also be incorporated into the compositions.

Oral dosage units can be tablets or capsules, for example. Other compositions for oral administration include elixirs, syrups, and the like.

Solutions of the active composition can be aqueous, optionally mixed with a nontoxic surfactant and/or can contain carriers or excipients, such as salts, carbohydrates and buffering agents (preferably at a pH of from 3 to 9), but, for some applications, they can be more suitably formulated as a sterile non-aqueous solution or as a dried form to be used in conjunction with a suitable vehicle, such as sterile, pyrogen-free water or phosphate-buffered saline. For example, dispersions can be prepared in glycerol, liquid PEGs, triacetin, and mixtures thereof and in oils. Under ordinary conditions of storage and use, these preparations can further contain a preservative to prevent the growth of microorganisms.

Excipients can include suspending agents, for example, sodium carboxymethylcellulose, methylcellulose, hydroxypropylmethylcellulose, sodium alginate, polyvinylpyrrolidone, gum tragacanth and gum acacia; dispersing or wetting agents, which can be a naturally occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions can also contain one or more preservatives, for example ascorbic acid, ethyl, n-propyl, or p-hydroxybenzoate; or one or more coloring agents.

Dispersible powders and granules suitable for preparation of an aqueous suspension by the addition of water can provide the active ingredient in admixture with a dispersing or wetting agent, suspending agent and one or more preservatives. Additional excipients, for example, coloring agents, can also be present.

Suitable emulsifying agents can be naturally occurring gums, for example, gum acacia or gum tragacanth; naturally occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. Isotonic agents, for example, sugars, polyalcohols, such as mannitol or sorbitol, or sodium chloride can be included in the composition. Prolonged absorption of injectable compositions can be brought about by including in the composition an agent which delays absorption, such as monostearate salts and gelatin.

Liquid formulations can include suspensions and solutions. Such formulations can comprise a carrier, for example, water, ethanol, polyethylene glycol, propylene glycol, methylcellulose, or a suitable oil, and one or more emulsifying agents and/or suspending agents. Liquid formulations can also be prepared by the reconstitution of a solid.

Still further provided is a method of treating a subject in need of treatment for HIV or SARS.

Also contemplated herein is one or more compounds described herein for use as a medicament for treating a patient in need of treatment of HIV or SARS.

The compound can be formulated as a pharmaceutical composition and administered to a subject, such as a mammal, e.g., a human, in a variety of forms adapted to the chosen route of administration as discussed above. For example, the composition can be administered as an oral dosage unit, an injectable composition (i.e., for subcutaneous or intravenous injection), or an infusion. See, e.g., Remington, supra.

An effective amount of the compound, or the pharmaceutical composition comprising the compound, can be determined in accordance with methods known in the art (e.g., animal models, human data, and human data for compounds that are used in a similar manner). The amount can be determined by taking into consideration various factors, such as the potency of the conjugate, body weight, mode of administration, the type and location of fracture, and its causation. The effective amount can range from about 0.1 pg/kg/day, such as 0.5 pg/kg/day, 0.7 pg/kg/day, or 0.01 mg/kg/day up to about 1,000 mg/kg/day. Intravenous doses can be several orders of magnitude lower. The compound/composition can be administered more than once, such as daily (1-3 or more times per day), weekly (including 1-3 or more times on a given day), bi-weekly (including 1-3 or more times on a given day), monthly (including 1-3 or more times on a given day), or bimonthly (including 1-3 or more times on a given day).

The terms "substituted," "substituent," and "functional group" refer to a group that can be or is substituted onto a molecule or onto another group (e.g., on an aryl or an alkyl group). Examples of substituents include, but are not limited to, a halogen (e.g., F, Cl, Br, and I), OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, —(CH$_2$)$_{0-2}$P(O)(OR)$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl, which can be mono- or independently multi-substituted.

The term "alkyl" and "alkylene" as used herein refers to substituted or unsubstituted straight chain and branched mono- or divalent alkyl groups and cycloalkyl groups having from 1 to 40 carbon atoms (C$_1$-C$_{40}$), 1 to about 20 carbon atoms (C$_1$-C$_{20}$), 1 to 12 carbons (C$_1$-C$_{12}$), 1 to 8 carbon atoms (C$_1$-C$_8$), or, in some embodiments, from 1 to 6 carbon atoms (C$_1$-C$_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and ante-isoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched mono- or divalent alkenyl groups and cycloalkenyl groups having at least one double bond and having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkenyl groups include those with from 1 to 8 carbon atoms such as —CH═CH—, —CH═CHCH$_3$, and —CH$_2$CH═CHCH$_2$— groups, wherein the double bonds can have an E- or Z-configuration. And when there are multiple bonds, each double bond can, independently, have an E- or a Z-configuration. Examples of branched alkenyl groups include, but are not limited to, —CH═C(CH$_3$)— and CH$_2$C═CH(CH$_3$) groups. Representative substituted alkenyl groups can be substituted one or more times with any of the groups listed herein, for example, amino, hydroxy, cyano, carboxy, nitro, thio, alkoxy, and halogen groups.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups can have any number of carbon atoms, e.g., 3 to 8 carbon atoms ($C_3$-$C_8$), 3 to 6 carbon atoms ($C_3$-$C_6$), and 4 to 8 carbon atoms ($C_4$-$C_8$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "cycloalkylalkyl" as used herein refers to substituted or unsubstituted alkyl groups as defined herein in which a hydrogen or carbon bond of an alkyl group as defined herein is replaced with a bond to a cycloalkyl group as defined herein. Representative cycloalkylalkyl groups include, but are not limited to, cyclopentylalkyl.

The term "alkylcycloalkyl" as used herein refers to substituted or unsubstituted cycloalkyl groups as defined herein in which a hydrogen of a cycloalkyl group as defined herein is replaced with a bond to an alkyl group as defined herein. Representative alkylcycloalkyl groups include, but are not limited to, alkylcyclopropyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. "Aryl" and the phrase "aryl group" includes fused ring species including those that include fused aromatic and non-aromatic groups. Accordingly, "aryl" and the phrase "aryl group" include groups of the formula:

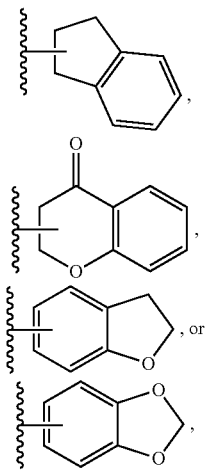

each of which can be substituted or unsubstituted, such as hydroxy substituted.

Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The terms "aralkyl" and "arylalkyl" refer to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" or "heterocyclo" refers to substituted or unsubstituted aromatic and non-aromatic ring compounds containing 3 or more ring members, of which one or more (e.g., 1, 2 or 3) is a heteroatom such as, but not limited to, N, O, and S. Thus, a heterocyclyl can be a cycloheteroalkyl or a heteroaryl or, if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise, a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds, such as in the group 3,6-dihydro-2H-pyran and 3,4-dihydro-2H-pyran, having the formula:

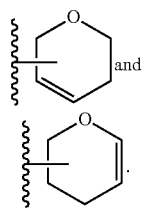

respectively, each of which can be substituted.

A heteroaryl ring is an embodiment of a heterocyclyl group. The phrase "heterocyclyl group" includes fused ring species including those that include fused aromatic and non-aromatic groups. Representative heterocyclyl groups include, but are not limited to tetrahydro-2H-thiopyran-1,1-dioxide, having the formula:

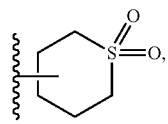

which can be substituted, 4a,5,6,7-tetrahydro-4H-pyrrolo[1,2-d][1,3,4]oxadiazinyl, having the formula:

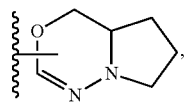

which can be substituted, pyrrolidinyl, pyrrolidinone (e.g., pyrrolidin-2-one), azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, imidazo[1,2-a]pyridinyl, having the formula:

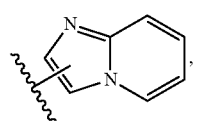

which can be substituted, triazyolyl, tetrazolyl, benzoxazolinyl, thiazolyl, benzthiazolinyl, and benzimidazolinyl groups. Examples of indolinonyl groups include groups having the general formula:

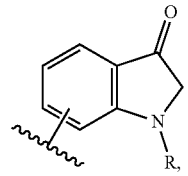

wherein R is as defined herein.

Examples of isoindolinonyl groups include groups having the general formula:

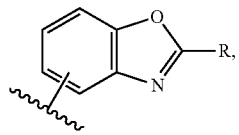

wherein R is as defined herein.

Examples of benzoxazolinyl groups include groups having the general formula:

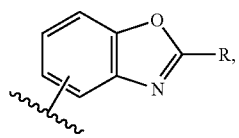

wherein R is as defined herein.

Examples of benzthiazolinyl groups include groups having the general formula:

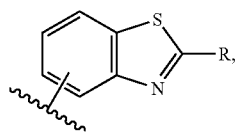

wherein R is as defined herein.

In some embodiments, the group R in benzoxazolinyl and benzthiazolinyl groups is an $N(R)_2$ group. In some embodiments, each R is hydrogen or alkyl, wherein the alkyl group is substituted or unsubstituted. In some embodiments, the alkyl group is substituted with a heterocyclyl group (e.g., with a pyrrolidinyl group).

The term "heterocyclylalkyl" refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heterocyclylalkoxy" refers to alkyl groups as defined herein in which a hydrogen or carbon bond of an alkyl group as defined herein is replaced with a bond to a heterocyclyl group as defined herein and the alkyl group is attached to an oxygen. Representative heterocyclylalkoxy groups include, but are not limited to, —O—(CH$_2$)$_q$ heterocyclyl, wherein q is an integer from 1 to 5. In some embodiments, heterocyclylalkoxy groups include —O—(CH$_2$)$_q$ morpholinyl such as —O—CH$_2$CH$_2$-morpoline.

The term "heteroarylalkyl" refers to alkyl groups as defined herein in which a hydrogen or carbon bond of an alkyl group is replaced with a bond to a heteroaryl group as defined herein.

The term "alkoxy" refers to an oxygen atom connected to an alkyl group, including a cycloalkyl group, as are defined herein. Examples of linear alkoxy groups include, but are not limited to, methoxy, ethoxy, propoxy, butoxy, pentyloxy, hexyloxy, and the like. Examples of branched alkoxy include, but are not limited to, isopropoxy, sec-butoxy, tert-butoxy, isopentyloxy, isohexyloxy, and the like. Examples of cyclic alkoxy include, but are not limited to, cyclopropyloxy, cyclobutyloxy, cyclopentyloxy, cyclohexyloxy, and the like. An alkoxy group can include one to about 12-20 or about 12-40 carbon atoms bonded to the oxygen atom, can further include double or triple bonds, and can also include heteroatoms.

For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "amine," "amine group," "amino," and "amino group" refer to a substituent of the form —NH$_2$, —NHR, —NR$_2$, or —NR$_3^+$, wherein each R is defined herein, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group.

An "alkylamino" group includes a monoalkylamino, dialkylamino, and trialkylamino group. An example of a "alkylamino" is —NH-alkyl and —N(alkyl)$_2$.

An example of a "cycloalkylamino" group is —NH-cycloalkyl and —N(cycloalkyl)$_2$.

An example of a "cycloalkyl heterocycloamino" group is —NH-(heterocyclo cycloalkyl), wherein the heterocyclo group is attached to the nitrogen and the cycloalkyl group is attached to the heterocyclo group.

An example of a "heterocyclo cycloamino" group is —NH-(cycloalkyl heterocycle), wherein the cycloalkyl group is attached to the nitrogen and the heterocyclo group is attached to the cycloalkyl group.

The term "amido" refers to a group of the formula —C(O)NR$^2$, wherein R is defined herein.

The terms "halo," "halogen," and "halide" group, by themselves or as part of another substituent, mean, unless otherwise stated, a fluorine, chlorine, bromine, or iodine atom.

The term "haloalkyl" group includes mono-halo alkyl groups, poly-halo alkyl groups, wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound, which contains a basic or acidic moiety, by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, the disclosure of which is hereby incorporated by reference for its teachings regarding same.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery,* 6th ed. (Donald J. Abraham ed., 2001, Wiley), and *Design and Application of Prodrugs* (H. Bundgaard ed., 1985, Harwood Academic Publishers GmbH).

Those skilled in the art will appreciate that many modifications to the embodiments described herein are possible without departing from the spirit and scope of the present disclosure. Thus, the description is not intended and should not be construed to be limited to the examples given but should be granted the full breadth of protection afforded by the appended claims and equivalents thereto. In addition, it is possible to use some of the features of the present disclosure without the corresponding use of other features. Accordingly, the foregoing description of or illustrative embodiments is provided for the purpose of illustrating the principles of the present disclosure and not in limitation thereof and can include modification thereto and permutations thereof.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "substantially no" as used herein refers to less than about 30%, 25%, 20%, 15%, 10%, 5%, 3%, 2%, 1%, 0.5%, 0.1%, 0.05%, 0.001%, or at less than about 0.0005% or less or about 0% or 0%.

Those skilled in the art will appreciate that many modifications to the embodiments described herein are possible without departing from the spirit and scope of the present disclosure. Thus, the description is not intended and should not be construed to be limited to the examples given but should be granted the full breadth of protection afforded by the appended claims and equivalents thereto. In addition, it is possible to use some of the features of the present disclosure without the corresponding use of other features. Accordingly, the foregoing description of or illustrative embodiments is provided for the purpose of illustrating the principles of the present disclosure and not in limitation thereof and can include modification thereto and permutations thereof.

Examples

The disclosure can be better understood by reference to the following examples which are offered by way of illustration. The disclosure is not limited to the examples given herein.

General Methods. All chemical and reagents were purchased from commercial suppliers and used without further purification unless otherwise noted. Solvents were purified as follows: $CH_2Cl_2$ was distilled from calcium hydride or purified using a solvent purification system; methanol was used without further purification; tetrahydrofuran (THF) was distilled from sodium/benzophenone. The flasks were fitted with rubber septa and kept under a positive pressure of argon.

Heated reactions were run using an oil bath on a hot plate equipped with a temperature probe. TLC analysis was conducted using glass-backed, thin-layer silica gel chromatography plates (60 Å, 250 µm thickness, F-254 indicator). Flash chromatography was done using a 230-400 mesh, 60 Å pore diameter silica gel. $^1H$ NMR spectra were recorded on 400 and 500 MHz spectrometers. $^{13}C$ NMR spectra were recorded at 100 MHz NMR. Chemical shifts are reported in parts per million and referenced to the deuterated, residual solvent peak ($CDCl_3$, 7.26 ppm for $^1H$ and 77.16 ppm for $^{13}C$). NMR data are reported as δ value (chemical shift), J-value (Hz), and integration, where s=singlet, bs=broad singlet, d=doublet, t=triplet, q=quartet, p=quintet, m=multiplet, dd=doublet doublets, and so on.

Optical rotations were recorded on a digital polarimeter. Low resolution mass spectra (LRMS) spectra were recorded using a quadrupole LCMS under positive electrospray ionization (ESI+). High-resolution mass spectrometry (HRMS) spectra were recorded at the Purdue University Department of Chemistry Mass Spectrometry Center. These experiments were performed under ESI+ and positive atmospheric pressure chemical ionization (APCI+) conditions using an Orbitrap XL Instrument.

Preparation of carboxylic acid 7. Methanol (3.66 mL, 0.090 mol) was added to a stirred solution of the anhydride 6 (4.92 g, 0.030 mol) and quinidine/quinine (10.71 g, 0.033 mol) in a 1:1 mixture of toluene and $CCl_4$ (150 mL in the case of quinidine, 600 mL in the case of quinine) at −55° C. under an argon atmosphere. The reaction mixture was stirred at this temperature for 60 hours during which the material gradually dissolved. Subsequently, the resulting clear solution was concentrated in vacuo to dryness, and the resulting residue was then dissolved in ethyl acetate. The solution was washed with 1N HCl and, after phase separation, the aqueous phases were extracted with ethyl acetate (×3), and the organic layer was dried over $Na_2SO_4$, filtered, and concentrated to provide the corresponding cis-monoester 7 as an amorphous solid (5.10 g, 86%).

Preparation of alcohol 8. Methyl chloroformate (1.33 g, 12.3 mmol) was added dropwise to a solution of 7 (2.03 g, 10.2 mmol) and triethylamine (1.35 g, 13.3 mmol) in THF (20 mL) at 0° C. The reaction mixture was stirred at 0° C. for 1 hour and concentrated to a half volume under reduced pressure. A solution of sodium borohydride (775 mg, 20.5 mmol) in $H_2O$ (10 mL) was added to the resulting mixture at 0° C. The reaction mixture was stirred for 20 minutes at the same temperature. The solvent was evaporated under reduced pressure. The residue was neutralized by adding saturated $NH_4Cl$ solution and extracted with ethyl acetate (EtOAc). The organic layer was dried over $Na_2SO_4$ and concentrated in vacuo, and the resulting residue was purified by flash chromatography on silica (25% EtOAc/hexanes to 40% EtOAc/hexane) to yield the 8 (970 mg, 51%). $^1$H-NMR (400 MHz, CDCl$_3$) δ 6.20 (dd, 1H), 6.09 (dd, 1H), 3.63 (d, 3H), 3.53-3.44 (m, 1H), 3.39 (dd, 1H), 3.13 (dd, 2H), 2.88 (dp, 2H), 2.75-2.63 (m, 1H), 1.51-1.39 (m, 1H), 1.39-1.31 (m, 1H). $^{13}$C NMR (100 MHz, CDCl$_3$) δ 174.86, 135.78, 134.60, 63.96, 51.51, 48.71, 47.21, 46.95, 46.23, 45.72.

Preparation of methyl ester 10. The above alcohol 8 was taken up in CH$_2$Cl$_2$ (20.0 mL) and cooled to −78° C., and a stream of O$_3$ was bubbled through the solution until a blue color persisted. Upon consumption of the starting material, argon was bubbled through the blue solution until the solution became clear. Dimethyl sulfide (0.13 mL, 1.75 mmol) was added to the reaction, and the mixture was warmed to room temperature and stirred an additional 14 hours. The crude product was used in the next step without further purification.

To a flask containing the above crude hemiacetal 9 (2.3 g, 6.3 mmol) in dry CH$_2$Cl$_2$ (20 mL) at −10° C. was added trifluoroacetic acid (TFA; 6.18 mL, 50.5 mmol) dropwise over 5 minutes, and then triethylsilane (TES; 3.01 mL, 18.9 mmol) was added. The reaction mixture was stirred at −10° C. to 23° C. for 6 hours. The reaction mixture was cooled to 0° C., quenched with a saturated solution of NaHCO$_3$ (20 mL), and extracted with (3×) CH$_2$Cl$_2$. The combined organic layer was washed with water and brine. The organic solution was dried over anhydrous Na$_2$SO$_4$, filtered, and concentrated under reduced pressure. The product was purified by silica gel column chromatography (20% EtOAc/hexane) to afford 10 as oil (1.44 g, 87%). $^1$H-NMR (400 MHz, CDCl$_3$) δ 5.44 (d, 1H), 4.14 (dd, 1H), 4.00 (dd, 1H), 3.97-3.81 (m, 2H), 3.70 (s, 3H), 3.05-2.94 (m, 1H), 2.96-2.88 (m, 1H), 2.75 (tdd, 1H), 2.62-2.49 (m, 1H), 1.94 (s, 1H), 1.43 (dt, 1H). $^{13}$C NMR (101 MHz, CDCl$_3$) δ 172.50, 104.08, 72.18, 63.37, 51.41, 50.94, 45.02, 41.15, 36.34, 27.38.

Preparation of alcohol 11. Diisobutyl aluminum hydride (1 M in CH$_2$Cl$_2$, 27.5 mL, 27.5 mmol) was slowly added to a solution of ester 10 (5.5 g, 27.5 mmol) in THF (100.0 mL) at −78° C. The solution was allowed to stir for 2 hours at −78° C. A saturated solution of sodium potassium tartrate (20 mL) was added, and the reaction mixture was warmed to room temperature. The reaction was stirred until both layers were transparent. The organic layer was separated, and the aqueous layer was extracted with EtOAc (3×). The organic layers were combined, washed with brine, and dried over Na$_2$SO$_4$. The solid was filtered out, the organic layer was concentrated under vacuum, and the product was purified by silica gel column chromatography (50% EtOAc/hexane) to afford alcohol 11 as oil (1.44 g, 87%). $^1$H-NMR (400 MHz, CDCl$_3$) δ 5.39 (d, 1H), 4.10 (d, 1H), 3.86 (d, 2H), 3.81-3.62 (m, 3H), 2.76-2.56 (m, 2H), 2.34-2.11 (m, 2H), 1.88 (d, 1H), 1.79 (s, 1H), 1.49 (dtd, 1H). $^{13}$C NMR (100 MHz, CDCl$_3$) δ 103.95, 68.82, 61.72, 60.12, 45.47, 44.60, 36.19, 27.48.

Preparation of alkene 12. To a solution of alcohol 11 (679 mg, 4.29 mmol) in CH$_2$Cl$_2$ (25 mL) at 0° C. was added sequentially N,N-diisopropylethylamine (DIPEA; 288 mg, 2.57 mmol), and mesyl chloride (982 mg, 5.15 mmol). After stirring the solution for 7 minutes at 0° C., the reaction mixture was quenched with water and extracted with (3×) CH$_2$Cl$_2$. The combined organic layer was washed with water and brine. The organic solution was dried over anhydrous Na$_2$SO$_4$, filtered, and concentrated under reduced pressure. The product was purified by silica gel column chromatography (30% EtOAc/hexane) to afford the corresponding mesylate as oil (1.44 g, 87%). $^1$H-NMR (400 MHz, CDCl$_3$) δ 5.39 (d, 1H), 4.43 (d, 2H), 4.01 (d, 1H), 3.83-3.63 (m, 3H), 3.01 (s, 3H), 2.79-2.60 (m, 2H), 2.52-2.21 (m, 2H), 1.90 (d, 1H), 1.52 (dt, 1H). $^{13}$C NMR (100 MHz, CDCl$_3$) δ 103.69, 68.34, 67.83, 61.28, 45.58, 41.60, 40.96, 37.22, 36.41, 27.42.

In a sealed tube, the above mesylate (295 mg, 0.95 mmol) was dissolved in 1,2-dimethoxyethane (6 mL), and sodium iodide (427 mg, 2.85 mmol) was added. The solution turned yellowish orange. 1,8-diazabicyclo(5.4.0)undec-7-ene (DBU; 284 μL, 1.9 mmol) was added, and the mixture was heated in the sealed tube at 90° C. for 3 hours. The reaction was then cooled to room temperature, diluted with diethyl ether and water, and stirred for 10 minutes. The layers were separated, and the aqueous phase was extracted with diethyl ether (×2). The combined organic layers were washed with brine, dried over sodium sulfate, filtered, and concentrated in vacuo while keeping the water bath temperature below 5° C. The product was purified by silica gel column chromatography (20% diethyl ether/hexane) to afford volatile olefin 12 as oil (1.44 g, 87%). $^1$H-NMR (400 MHz, CDCl$_3$) δ 5.53 (d, 1H), 5.05 (dd, 1H), 4.88 (dd, 1H), 4.12 (dd, 1H), 4.03-3.85 (m, 2H), 3.68 (d, 1H), 3.02-2.87 (m, 1H), 2.79-2.68 (m, 1H), 2.61 (t, 1H), 1.91 (dd, 1H), 1.70-1.55 (m, 1H). $^{13}$C NMR (100 MHz, CDCl$_3$) δ 159.49, 106.75, 104.39, 76.06, 69.10, 46.12, 45.09, 42.94, 27.14.

Synthesis of ligand alcohol 3. A solution of alkene 12 (335 mg, 2.39 mmol) in CH$_2$Cl$_2$ (20 mL) was cooled to −78° C. Ozonized oxygen was bubbled through the mixture until the solution turned blue. The ozone flow was stopped, and oxygen was bubbled until the solution was colorless. The flask was then flushed with argon. Dimethyl sulfide (0.13 mL, 1.75 mmol) was added to the reaction, and the mixture was warmed to room temperature and stirred an additional 14 hours. The mixture was diluted with CH$_2$Cl$_2$ and washed with saturated aqueous sodium bicarbonate. The aqueous layer was extracted with CH$_2$Cl$_2$ (×3). The combined organic layers were washed with water and brine and dried with sodium sulfate. The solvent was evaporated to furnish the crude ketone 13 (298 mg, 88%) as a white amorphous solid. a 0.5 (50% ethyl acetate/hexanes).

To a solution of the above crude ketone (241 mg, 1.7 mmol) in ethanol (10 mL) was added sodium borohydride (128 mg, 3.4 mmol) at 0° C. The reaction mixture was allowed to warm to room temperature and stirred for 15 minutes. The ethanol was then removed under reduced pressure. The residue was purified by chromatography over silica gel (45% diethyl ether/pentane) to yield ligand alcohol 3 (220 mg, 90%) as a white amorphous solid. $[α]^D_{22}$ −9.33 (c 1.8, CHCl$_3$); Lit[1,2][α]$^D_{22}$ −9.27 (c 1.03, CHCl$_3$); $^1$H-NMR (400 MHz, CDCl$_3$) δ 5.45 (d, 1H), 4.42 (dd, 1H), 4.32-4.20 (m, 1H), 4.06 (d, 1H), 3.75 (dd, 1H), 3.66 (dd, 1H), 2.74-2.60 (m, 2H), 2.24 (q, 1H), 1.82 (d, 1H), 1.64 (s, 2H), 1.55-1.42 (m, 1H). $^{13}$C NMR (100 MHz, CDCl$_3$) δ 104.16, 72.34, 67.92, 59.15, 45.05, 42.73, 39.16, 23.64.

Synthesis of 4-nitrophenyl carbonate 14. Synthesis of carbonate was carried out using a previously published procedure. [1,2] To a flame-dried flask were added optically active Crown-THF alcohol 3 (6 mg, 0.046 mmol) and CH$_2$Cl$_2$ (1.0 mL) followed by addition of pyridine (7.5 μL, 0.092 mmol). The mixture was stirred under argon and cooled to 0° C. To the mixture was quickly added 4-nitrophenyl chloroformate (19 mg, 0.092 mmol), and the resulting reaction was stirred at 23° C. for 12 hours. After this period, the mixture was concentrated under reduced pressure and purified by flash chromatography (35% EtOAc/hexanes) to yield carbonate 14 (12 mg, 92% yield) as an amorphous white solid. $^1$H-NMR (400 MHz, CDCl$_3$) δ 8.29 (d, 2H), 7.39 (d, 2H), 5.52 (d, 1H), 5.02 (dd, 1H), 4.28 (dd, 1H), 4.06 (d, 1H), 3.86 (dd, 1H), 3.75 (dd, 1H), 3.02-2.90 (m, 1H), 2.79 (td, 1H), 2.60 (t, 1H), 1.95 (d, 1H), 1.64-1.50 (m, 2H). $^{13}$C NMR (100 MHz, CDCl$_3$) δ 155.24, 151.93, 145.40, 125.29, 121.64, 104.32, 79.64, 68.32, 59.44, 44.88, 41.72, 37.28, 23.45.

Preparation of protease inhibitor 2. To a stirred solution of activated crown-THF carbonate 14 (26 mg, 0.08 mmol) and previously known[24] amine 4 (51 mg, 0.09 mmol) in acetonitrile (2 mL) was added DIPEA (71 μL, 0.4 mmol) at 23° C. under argon atmosphere. The reaction mixture was stirred at 23° C. until completion. Upon completion, solvents were removed under reduced pressure, and crude product was purified by silica gel column chromatography (55% EtOAc in hexane) to give inhibitor 2 (48 mg, 84% yield). $^1$H NMR (500 MHz, CDCl$_3$) δ 8.27 (s, 1H), 8.10-8.07 (m, 1H), 7.73-7.67 (m, 1H), 7.52 (d, J=8.5 Hz, 1H), 6.76 (d, J=6.3 Hz, 2H), 6.61 (t, J=8.9 Hz, 1H), 5.84 (d, J=9.2 Hz, 1H), 5.41 (d, J=6.7 Hz, 1H), 4.82 (dd, J=8.9, 5.8 Hz, 1H), 4.16 (brs, 1H), 3.98-3.92 (m, 1H), 3.85 (dt, J=12.6, 6.1 Hz, 3H), 3.60 (dd, J=9.0, 6.5 Hz, 1H), 3.54 (dd, J=11.1, 7.9 Hz, 1H), 3.17-3.11 (m, 2H), 3.06 (dd, J=14.0, 3.4 Hz, 1H), 2.96 (dd, J=13.3, 8.0 Hz, 1H), 2.89 (dd, J=13.4, 7.1 Hz, 1H), 2.79 (dd, J=13.9, 10.5 Hz, 1H), 2.75-2.68 (m, 2H), 2.67-2.61 (m, 1H), 2.34-2.27 (m, 1H), 1.86 (dp, J=14.5, 6.9 Hz, 1H), 1.78 (d, J=11.9 Hz, 1H), 1.43 (dd, J=8.0, 4.0 Hz, 1H), 0.93 (t, J=6.7 Hz, 2H), 0.87 (dd, J=12.6, 7.1 Hz, 6H), 0.79-0.75 (m, 2H); $^{13}$C NMR (125 MHz, CDCl$_3$) δ 173.7, 163.9 (d, J=12.7 Hz), 161.9 (d, J=12.8 Hz), 155.7 (d, J=18.0 Hz), 142.4 (t, J=8.8 Hz), 131.1, 130.2, 125.5, 121.0, 118.2, 112.5-112.0 (m), 104.3, 102.0 (t, J=25.1 Hz), 74.8, 72.9, 68.3, 59.9, 58.8, 55.1, 53.5, 44.9, 42.2, 37.4, 31.6, 27.3, 26.7, 23.6, 22.7, 20.2, 20.0, 7.8; HRMS-ESI (m/z): [M+H]$^+$ calcd for $C_{33}H_{41}F_2N_4O_7S_2$, 707.2385; found 707.2379.

What is claimed is:

1. A method of making a compound of the formula (I):

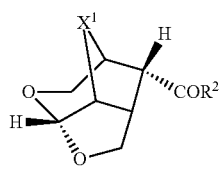

(I)

or a salt thereof, with an enantiomeric excess (ee) of at least 90%;
wherein:
$X^1$ is alkylene, —O—, —CH$_2$NR$^1$— or —NHR$^1$—, wherein R$^1$ is alkyl, aryl or heteroaryl, and
R$^2$ is hydroxy, alkoxy or amido;
the method comprising
(i) converting a compound of the formula (II):

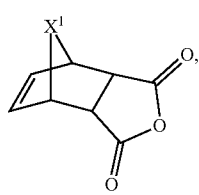

(II)

or a salt thereof, to a compound of the formula (III):

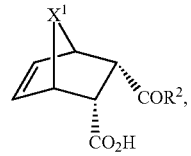

(III)

or a salt thereof;

(ii) converting the compound of formula (III), or a salt thereof, to a compound of the formula (IV):

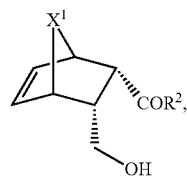

(IV)

or a salt thereof; and (iii) converting the compound of formula (IV), or a salt thereof, to the compound of the formula (I).

2. The method of claim 1, wherein the converting in step (i) comprises ring opening of the compound of the formula (II).

3. The method of claim 1, wherein the converting in step (ii) comprise reducing the compound of formula (III) to a compound of the formula (IV), or a salt thereof.

4. The method of claim 1, wherein the converting in step (iii) comprises ozonolysis of the compound of formula (IV), or a salt thereof, to give an ozonolysis product, or a salt thereof.

5. The method of claim 4, further comprising reducing the ozonolysis product, or a salt thereof, to obtain the compound of the formula (I).

6. The method of claim 4, wherein the ozonolysis product is of the formula (V):

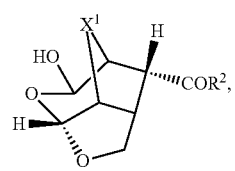

(V)

or a salt thereof.

7. The method of claim 1, wherein $X^1$ is alkylene.

8. The method of claim 7, wherein alkylene is a $C_1$-$C_3$ (alkylene) group.

9. The method of claim 8, wherein the alkylene is —CH$_2$—.

10. The method of claim 1, wherein $X^1$ is alkylene and $R^2$ is hydroxy.

11. A method of making a compound of the formula (VI):

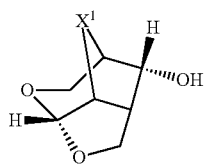

(VI)

or a salt thereof, with an enantiomeric excess (ee) of at least 90%;
wherein:
$X^1$ is alkylene, —O—, —$CH_2NR^1$— or —$NHR^1$—, wherein $R^1$ is alkyl, aryl or heteroaryl;
the method comprising:
(i) converting a compound of the formula (I):

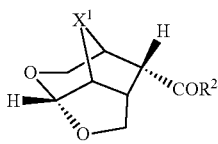

(I)

or a salt thereof,
wherein:
$X^1$ is alkylene, —O—, —$CH_2NR^1$— or —$NHR^1$—, wherein $R^1$ is alkyl, aryl or heteroaryl, and
$R^2$ is hydroxy, alkoxy or amido,
to a compound of the formula (VII):

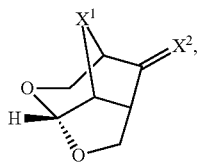

(VII)

or a salt thereof, wherein $X^2$ is O or $CH_2$; and
(ii) converting the compound of formula (VII), or a salt thereof, to a compound of the formula (VI), or a salt thereof.

12. The method of claim 11, further comprising (iii) converting the compound of the formula (I) to a compound of the formula (VIII):

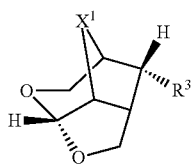

(VIII)

or a salt thereof,
wherein:
$X^1$ is alkylene —O—, —$CH_2NR^1$— or —$NHR^1$—, wherein $R^1$ is alkyl, aryl or heteroaryl, and
$R^3$ is hydroxyalkyl or $COR^2$, wherein $R^2$ is hydroxy, alkoxy or amido; and (iv) converting the compound of the formula (VIII) to the compound of the formula (VII), wherein $X^2$ is $CH_2$.

13. The method of claim 12, wherein $R^3$ is —$CH_2OH$.

14. The method of claim 12, further comprising (v) converting the compound of the formula (VII), or a salt thereof, wherein $X^2$ is $CH_2$ to the compound of the formula (VII), or a salt thereof, wherein $X^2$ is O.

15. The method of claim 11, wherein $X^1$ is alkylene.

16. The method of claim 14, wherein alkylene is a $C_1$-$C_3$ (alkylene) group.

17. The method of claim 15, wherein the alkylene is —$CH_2$—.

18. The method of claim 11, further comprising (vi) converting the compound of formula (VI), or a salt thereof, to a compound of the formula (IX):

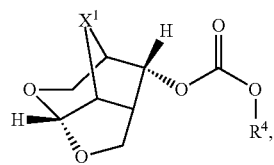

(IX)

or a salt thereof, wherein $R^4$ is optionally substituted aryl.

19. The method of claim 18, further comprising conjugating the compound of the formula (IX), or a salt thereof, with a compound of the formula (X):

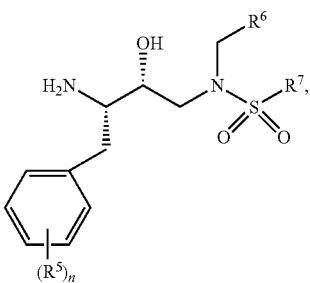

or a salt thereof, wherein:
n is an integer from 1 to 3;
$R^5$ is alkoxy, hydroxyalkyl, halo or heterocyclylalkyloxy;
$R^6$ is alkyl, haloalkyl, arylalkyl, cycloalkylalkyl, heterocyclylcarbonyl or heterocyclylalkyl; and
$R^7$ is aryl or heteroaryl, to give a compound of the formula (XI):

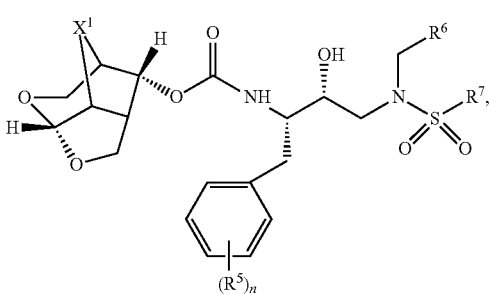

or a salt thereof.

20. A method of making a compound of the formula (VIII):

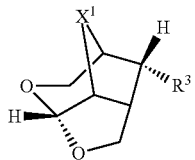
(VIII)

or a salt thereof, with an enantiomeric excess (ee) of at least 90%;
wherein:
$X^1$ is alkylene —O—, —$CH_2NR^1$— or —$NHR^1$—, wherein $R^1$ is alkyl, aryl or heteroaryl, and
$R^3$ is hydroxyalkyl or $COR^2$, wherein $R^2$ is hydroxy, alkoxy or amido;

the method comprising:
(i) converting a compound of the formula (I):

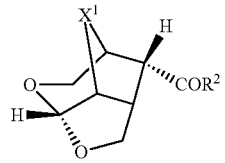
(I)

or a salt thereof,
wherein:
$X^1$ is alkylene —O—, —$CH_2NR^1$— or —$NHR^1$—, wherein $R^1$ is alkyl, aryl or heteroaryl; and
$R^2$ is hydroxy, alkoxy or amido,
to a compound of the formula (VIII).

* * * * *